(12) United States Patent
Li et al.

(10) Patent No.: US 7,387,801 B2
(45) Date of Patent: Jun. 17, 2008

(54) **ORGANIC EXTRACT OF *GEUM JAPONICUM THUNB* VARIANT AND USE THEREOF**

(75) Inventors: Ming Li, Hong Kong (CN); Jao Yiu Sung, Shatin (CN); Ping Chung Leung, Hong Kong (CN); Hui Dong, Shatin New Territory (CN); Kai Ming Chan, Taipo (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 10/538,433

(22) PCT Filed: Dec. 10, 2002

(86) PCT No.: PCT/CN02/00878

§ 371 (c)(1),
(2), (4) Date: Jan. 23, 2006

(87) PCT Pub. No.: WO2004/052381

PCT Pub. Date: Jun. 24, 2004

(65) Prior Publication Data

US 2006/0134229 A1    Jun. 22, 2006

(51) Int. Cl.
*A61K 36/00* (2006.01)
(52) U.S. Cl. ..................................... 424/725
(58) Field of Classification Search ........................ None
See application file for complete search history.

(56) References Cited

U.S. PATENT DOCUMENTS 5,916,919 A * 6/1999 Xu et al. ..................... 514/557

FOREIGN PATENT DOCUMENTS

JP    03190809 A *  8/1991
JP    7-179347       7/1995

OTHER PUBLICATIONS

1998. Dong et al. Effects of Tannins from *Geum japonium* on the Catalytic Activity of Thrombin and factor Xa of Blood Coagulation Cascade. J. Natural products. 61. 1356-1360.*
Kumar et al.: Fibrous Lesions of Bones.: RadioGraphics. 1990. 10; 237-256.*

* cited by examiner

*Primary Examiner*—Christopher R. Tate
*Assistant Examiner*—Melenie McCormick
(74) *Attorney, Agent, or Firm*—Merchant & Gould P.C.

(57) ABSTRACT

An organic extract of a Chinese herbal medicine *Geum Japonicum thunb* var. has been identified that displayed potent stimulatory effects on rapid agiogenesis (<24 h), myogenesis and blocking fibrosis in traumatized skeletal muscles. The extract has displayed potent dual effects on angiogenesis and myogenesis in damaged skeletal muscles leading to complete skeletal muscle healing in rabbit and rat animal models. The extract of the present invention can be developed into an effective therapeutic drug for the treatment of skeletal muscle trauma, soft tissue healing including burn, skin wound and operation cut, and bone fracture and defect healings.

3 Claims, 3 Drawing Sheets

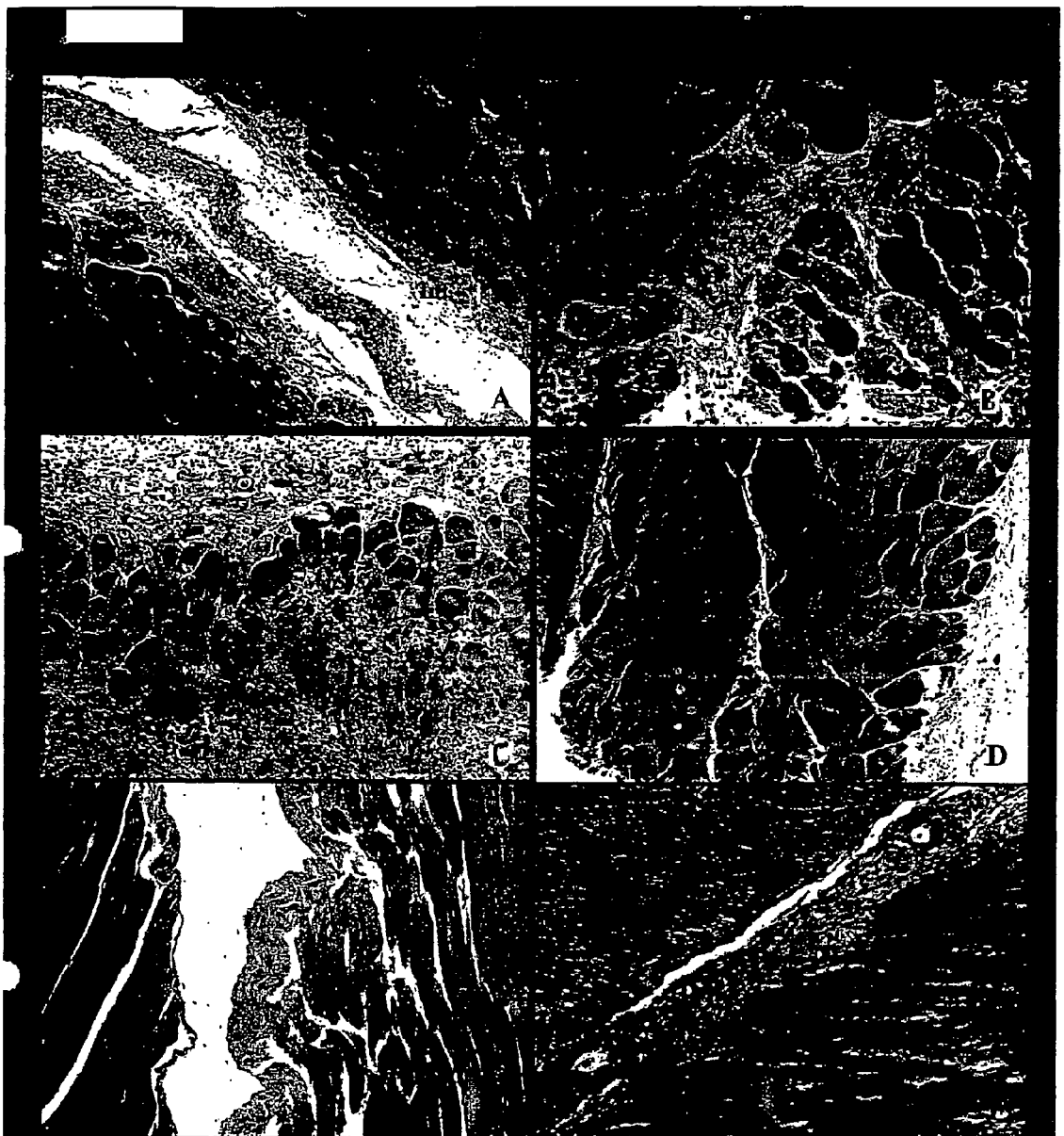

Fig. 1 The appearance of strain injured rabbit tibialis anterior following treatment with EGJV. The wound site was filled with a lot of inflammatory cells (A) and some newly formed blood vessels with a few newly regenerated myotubes were also found in the wound site on day 1 (B). Many newly formed blood vessels were observed in the wound site and some newly regenerated myotubes were also formed (C) 2 days after the muscle injury. In contrast, the wound site was still fresh and there were almost no infiltration of inflammatory cells in DMSO control group (E). Many newly regenerated and relatively matured myotubes sized a bit smaller than normal myofibers with central nuclei were observed in the gap of wound on day 18 in EGJV treated group (D). In contrast, the gap of wound in control was filled with fibrous tissue (F).

Fig. 2: The appearance of strain injured rat tibialis anterior following treatment with EGJV for 1, 2 and 3 days. a, The wound site was filled with a lot of inflammatory cells (Inf) in 5% DMSO control on day 2. N indicates the appearance of normal muscle fibers. In contrast, in EGJV treated group, many newly formed blood vessels were observed in the wound site (indicated by black arrows) 1 day after the muscle injury (b); in addition to many newly formed vessels indicated by black arrows and along the newly formed blood vessels many newly regenerated and elongated thin myotubes (indicated by green arrows) were observed on day two (c); many more newly regenerated myotube clusters as surrounded by green arrows were observed on day 3 (d).

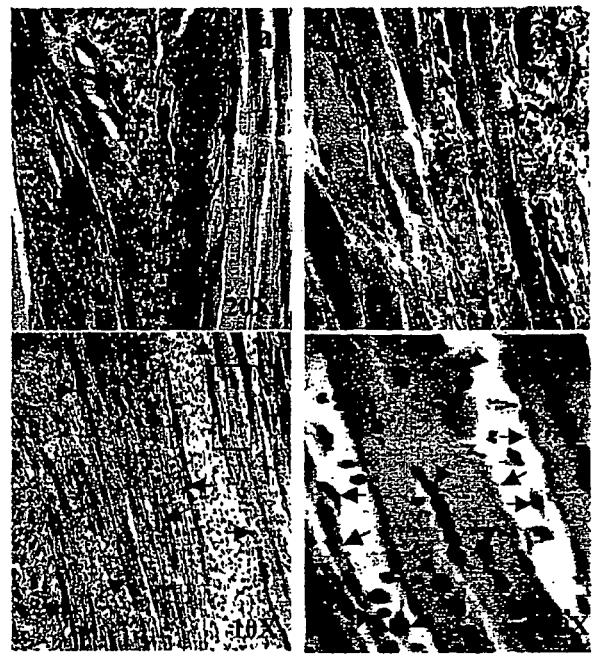

Fig. 3: The histological appearance of strain injured tibialis anterior following treatment with EGJV for 7 days. a, The wound site in control were full of inflammatory cells & fiberous tissues (Fb and Inf). b,c, In contrast, well-aligned & elongated newly regenerated myotubes (indicated by red arrows) were observed and they bridged the gaps of the wound sites in EGJV treated group. d, It is the amplified area in the blue rectangular in c. The red arrows indicate the newly regenerated myotubes, the green arrows indicate the central nuclei of the newly regenerated myotubes. The blue arrows suggest the activated satellite cells. Some of them were going to fuse with the myotubes.

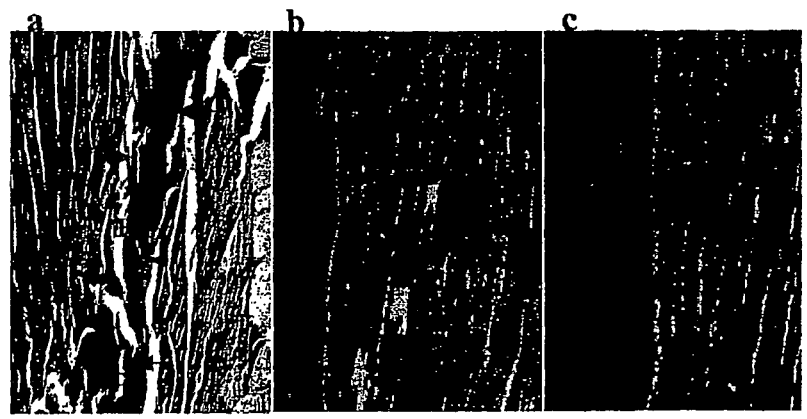

Fig. 4: The histological picture of strain injured tibialis anterior following treatment with EGJV for 14 days. a, The wound sites in control were healed with fibrosis (Fb) and the gaps of injuries were contracted (blue arrows). b,c, In contrast, well-aligned & elongated newly regenerated muscle fibers completely bridged the gaps of the wounds in EGJV treated group. Rm indicates the newly regenerated muscle fibers and Em shows the pre-existing muscle fibers. The contour of the cutting lines could still be recognized as indicated by arrows. The newly regenerated muscle fibers (less than two weeks old) are differently stained compared with the pre-existing muscle fibers probably due to the protein contents are still different in the two different aged cell groups.

ORGANIC EXTRACT OF *GEUM JAPONICUM THUNB* VARIANT AND USE THEREOF

PRIORITY INFORMATION

This application is a 371 national stage application of PCT/CN02/000878, filed Dec. 10, 2002.

TECHNICAL FIELD OF THE INVENTION

The present invention relates to Chinese Herbal Medicine. In particular, the present invention relates to an organic extract of *Geum Japonicum Thunb* variant (hereinafter referrec to as "EGJV") and use of the organic extract for stimulating neovascularization, skeletal muscle regeneration and inhibition of fibrosis in damaged skeletal muscles and soft tissues including skin. The present invention also relates to a method for preparing the organic extract of EGJV and a method for treating skeletal muscle injuries or skin injuries, enhancing the healing of operation cut, or reducing scar formation in skin healing and plastic surgeries.

BACKGROUND OF THE INVENTION

*Geum* is a genus of 65 species of rhizomatous herbs and subshrubs with simple or pinnately lobed leaves and regular flowers, such as *G. borisii, G. chiloense, G. coccineum, G. macrophyllum, G. montanum, G. reptans, G. rivale, G. triflorum, G. Urbanum*, and *G. Japonicum*, etc. *Geum japonicum Thunb* is a perennial herb and the flowering plant of the Rosaceae family. Water extract of the whole plant of *Geum japonicum Thunb* variant has been used as a diuretic in traditional Chinese medicine (Perry, L. M., *In Medicinal Plants of East and Southeast Asia*, MIT Press, Cambridge, Mass., pp. 242, 1980).

Skeletal-muscle healing following severe injury is slow and incomplete. The limited ability of damaged skeletal muscle to regenerate and the rapid formation of fibrous scar tissues at the wound site are major clinical problems. The common fate of severely traumatized skeletal muscle is fibrosis. To date, there is no effective therapeutic treatment that can promote complete skeletal muscle healing following severe injury.

As stated above, muscle healing following severe injury is slow and incomplete, resulting in fibrous tissue replacement (Grounds, M. D. Muscle regeneration: molecular aspects and therapeutic implications. *Curr. Opin. Neurol.* 12, 535-543 (1999); Nikolaou, P. K., et al., Biomechanical and histological evaluation of muscle after controlled strain injury. *American J Sports Med.* 15, 9-14(1987)). At present, there is no effective therapeutic measure that can be taken to promote significant skeletal muscle regeneration after severe muscle injury. In our previous studies (Li, M. et al., Two novel myogenic factors identified and isolated by sequential isoelectric focusing and sodium dodecyl sulfate-polyacrylamide gel electrophoresis. *Electrophoresis* 21, 289-292 (2000); Li, M., et al., Identification and purification of an intrinsic human muscle myogenic factor that enhances muscle repair and regeneration. *Arch. Biochem. Biophys.* 384, 263-268 (2000)), muscle myogenic factors that could enhance the proliferation and differentiation of cultured satellite cells as well as muscle fiber regeneration in animal models were identified. However, complete healing following severe muscle injury did not occur although these myogenic factors could improve muscle healing.

Fibrous tissue can grow in relative ischemic environment but normal tissue cells are difficult to grow. When the skeletal muscles are damaged, the vasculatures are often damaged and therefore blood supply around the damaged site is insufficient. Normally, fibrous tissue grows faster and occupies the space previously occupied by the damaged muscle fibers, then blocks the space for new muscle fiber replacement. According to previous studies, some growth factors, such as VEGF, aFGF, bFGF, or PDGF, could enhance angiogenesis, but this angiogenesis mediated by those growth factors may require approximately two to nine weeks. There is no product available in the world market that is capable of inducing complete healing of severely damaged skeletal muscles, especially inducing neovascularization rapidly in a mater of hours. Up to now there is no recorded any drug or any factors in market or even in research available that could lead complete healing of severely damaged skeletal muscles.

SUMMARY OF THE INVENTION

It is a principal object of the present invention to provide an agent capable of inducing complete healing of severely damaged skeletal muscles while inhibiting fibrosis of the damaged skeletal muscles. To accomplish this object, the present inventors have conducted diligent research. As a result, they have discovered that an organic extract from a natural source (the whole plant of *Geum Japonicum Thunb* Variant showed dual effects on rapid angiogenesis and myogenesis. These dual effects can be used for the treatment of skeletal muscle injuries, for other soft tissues healing, such as skin healing, operation cut healing, burn and ulcers, and for hard tissues healing, such as bone fracture healing and bone defect repairing.

One of the objects of the present invention is to provide the EGJV. The "EGJV" contains mainly tannins including gemins A, B, C, D, E and F and triterpenes including 2-hydroxyoleanolic acid, 2-hydroxylursolic acid, 2,19-dihydroxy-ursolic acid, 2-alpha,19-alpha-dihydroxy-3-oxo-12-ursen-28-oic acid, ursolic acid, epimolic acid, maslinic acid, euscaphic acid, tormentic acid, 28-beta-D-glucoside of tormentic acid and etc.

Another object of the present invention is to provide a use of the "EGJV" in preparation of a medicament for treating skeletal muscle injuries, skin injuries or bone fractures. The EGJV can, in combination with pharmaceutically acceptable additives, be formulated into various kinds of medicaments for treating skeletal muscle injuries, skin injuries or bone fractures.

Another object of the present invention is to provide a method for treating skeletal muscle injuries or skin injuries, comprising administrating to a mammal suffered from skeletal muscle injuries or skin injuries an effective amount of the "EGJV".

Another object of the present invention is to provide a method for preparing the "EGJV", comprising the step of extracting the plant of *Geum Japonicum Thunb* variant with C1-C4 alcohols.

These and other features of the present invention will be well understood by one skilled in the art from the following detailed description in view of the drawings.

BRIEF DESCRIPTION OF THE DRAWINGS

FIG. 1 shows the appearance of strain injured tibialis anterior of rabbits following treatment with the EGJV dissolved in 5% DMSO of the present invention or 5% DMSO control for 1, 2, 3, 7 and 18 days. FIG. 1A shows that the wound site was filled with a lot of inflammatory cells (Inf). The note "N" indicates the appearance of normal muscle fibers. FIG. 1B shows that upon treated with the EGJV, some new blood vessels with a few newly regenerated thin myotubes were observed in the wound site on day 1. The new blood vessels are indicated by black arrows and the newly regenerated myotubes were indicated by green arrows. As shown in FIG. 1C, many newly formed blood vessels were observed in the wound site (indicated by green arrows) and some newly regenerated myotubes were formed (indicated by black arrows) 2 days after the muscle injury. In contrast, as shown in FIG. 1E (DMSO control group), the wound site was still fresh and there were almost no infiltration of inflammatory cells. Neither newly formed blood vessels nor newly regenerated myotubes were observed.

Many newly regenerated and relatively matured myotubes (sizes a bit smaller than normal myofibers as indicated by N) with central nuclei were observed in the gap of wound on day 18 as indicated by black arrows (FIG. 1D). In contrast, the gap of wound in control was filled with fibrous tissue as indicated by "Fib" in FIG. 1F.

FIG. 2 is a photograph showing the appearance of strain injured tibialis anterior following treatment with the EGJV of the present invention for 1, 2 and 3 days. FIG. 2a shows that the wound site was filled with a lot of inflammatory cells (Inf) in 5% DMSO control on day 2. The note "N" indicates the appearance of normal muscle fibers. In contrast, from FIG. 2b-2d showing the result of EGJV treated group, many newly formed blood vessels were observed in the wound site (indicated by black arrows) 1 day after the muscle injury (Please refer to FIG. 2b). In addition to many newly formed blood vessels indicated by black arrows, many newly regenerated and elongated thin myotubes (indicated by green arrows) were observed along the newly formed blood vessels on day 2 after the muscle injury. (Please refer to FIG. 2c). And many more newly regenerated myotube clusters as surrounded by green arrows were observed on day 3 after the muscle injury. (Please see FIG. 2d).

FIG. 3 is a photograph showing the histological appearance of strain injured tibialis anterior in rat following treatment with EGJV for 7 days. FIG. 3a showed that the wound site in control were fall of inflammatory cells (indicated by "Inf") and fiberous tissues (indicated by "Fb"). In contrast, from FIG. 3b and 3c, well-aligned and elongated newly regenerated myotubes (indicated by red arrows) were observed and they bridged the gaps of the wound sites in EGJV treated group. FIG. 3d is the amplified area in the blue rectangular in FIG. 3c. The red arrows in FIG. 3d indicate the newly regenerated myotubes, the green arrows indicate the central nuclei of the newly regenerated myotubes and the blue arrows suggest the activated satellite cells. It can be seen that some of the satellite cells are going to fuse with the myotubes.

FIG. 4 is a photograph showing the histological appearance of strain-injured tibialis anterior following treatment with EGJV for 14 days. FIG. 4a showed that the wound sites in control were healed with fibrosis (indicated by "Fb") and the gaps of injuries were contracted (blue arrows). In contrast, from FIGS. 4b and 4c, it can be observed that well-aligned and elongated newly regenerated muscle fibers completely bridged the gaps of the wounds in EGJV-treated group. The note "Rm" indicates the newly regenerated muscle fibers and the note "Em" shows the pre-existing muscle fibers. The contour of the cutting lines could still be recognized as indicated by green arrows. In FIGS. 3b and 3c, the newly regenerated muscle fibers (less than two weeks old) are differently stained compared with the pre-existing muscle fibers probably due to the protein contents are still different in the two different aged cell groups.

DETAILED DESCRIPTION OF THE INVENTION

The present invention includes the following four aspects:
The first aspect relates to a method for preparing the EGJV.
1. A method for preparing an organic extract from Geum Japonicum Thunb var. is provided. This method comprises the step of a) extracting the plant of Geum Japonicum Thunb with alcohol selected from the group consisting of C1-C4 alcohols. The step of a) may repeat 3-6 times, preferably 5 times, at room temperature. Before performing the step of a), it is preferred to have the plant of *Geum Japonicum Thunb* powdered. The C1-C4 alcohols include methanol, ethanol, n-propanol, iso-propanol, n-butanol, iso-butanol, and ter-butanol. The more useful alcohol is methanol and ethanol. And methanol is the most preferred. There is no specific limitation with regard to the amount of the alcohols relative to the *Geum Japonicum thunb* var. to be extracted with the alcohols. However, from an economic view of point, the amount of alcohols to be used is preferably 1-10 times by weight of the amount of the *Geum Japonicum thunb* var. to be extracted.

2. The method as recited in the above item 1 may further comprise the step of b) drying the extract obtained from the step of a) into a dried powder; and c) successively extracting the powder obtained from the step of b) with C6 alkane, EtOAc and an alcohol selected from the group consisting of C1-C4 alcohols. The C6 alkane includes cyclic and non-cyclic alkane having 6 carbon atoms, including, for example, cyclohexane, n-hexane, and neo-hexane, etc. The C1-C4 alcohols include methanol, ethanol, n-propanol, iso-propanol, n-butanol, iso-butanol, and ter-butanol. The more useful alcohol in c) step is n-propanol and n-butanol. And n-butanol is the most preferred. There is no strict limitation with regard to the amount of the C6 alkane, EtOAc and alcohols relative to the dried powders obtained in the previous drying step. However, from an economic view of point, the amount of organic solvent to be used is preferably 1-10 times by weight of the amount of the powders to be further extracted.

3. To make the EGJV more applicable, the method as recited in the above item 2 may advantageously comprise the step of d) drying the extract obtained from the step of c) into dried powder. Before performing the drying step of d), it is preferred to filter the extract obtained from the previous step c) to remove any insoluble powders therein. The drying step of d) may complete under reduced pressure at a temperature higher than room temperature, for example, at 50° C.

4. To make the EGJV more purified, the method as recited in the above item 3 preferably further comprises the steps of e) applying the powder obtained from the step of d) onto a chromatographic column; and f) eluting the column with an aqueous solution with increasing concentration of an alcohol selected from the group consisting of C1-C4 alcohols. In step e), there is no limitation to the chromatographic column. For example, a Sephadex or reverse phase columns may be used. The alcohol used in the step of f) may be any one selected from the group consisting of methanol, ethanol, n-propanol, iso-propanol, n-butanol, iso-butanol, and ter-butanol. And methonal is the most preferred.

The second aspect of the present invention relates to an organic extract from Geum Japonicum thunb var., which is obtained by a method of any one as recited in above items 1-4. By NMR analysis, it is found that the EGJV of the present invention contains mainly tannins including gemin A, B, C, D, E and F and triterpenes including 2-hydroxyoleanolic acid, 2-hydroxylursolic acid, 2,19-dihydroxy-ursolic acid, 2-alpha,19-alpha-dihydroxy-3-oxo-12-ursen-28-oic acid, ursolic acid, epimolic acid, maslinic acid, euscaphic acid, tormentic acid, 28-beta-D-glucoside of tormentic acid.

The third aspect of the present invention relates to use of the organic extract from *Geum Japonicum Thunb* var. the preparation of a medicament for treating skeletal muscle injuries, skin injuries or bone fractures. The EGJV can be formulated into a medicament for enhancing angiogenesis and myogenesis. In addition to the EGJV, the medicament may comprise other pharmaceutical agents compatible with the EGJV. Said pharmaceutical agents include but not limit to drugs such as antibiotics, vitamins, cytokines and oesteoinductive proteins, etc. With pharmaceutically acceptable additives, the EGJV may be formulated into various forms, including but not limited to powder, solution, suspension, cream and paste, etc. The additives and methods for making those various forms of medicament are well known to the skilled person in the art.

The fourth aspect of the present invention relates to a method for treating skeletal muscle injuries, skin injuries or bone fractures, comprising administrating to ananimal suffered from skeletal muscle injuries, skin injuries, operation cut or bone fractures an effective amount of the organic extract from *Geum Japonicum thunb* var. The term "an effective amount" is an amount, which can effectively enhance angiogenesis and myogenesis in cell culture systems or in an animal model system. Such "an effective amount" depends on several factors including the species of the animal to be treated, the concentration of the EGJV to be administrated and the severity of the damages of the muscles or skins. Methods of determining such "an effective amount" is well known to an ordinary person skilled in the art. The term "administrating" used herein means any of standard routes for delivering a medicament. The route of administrating is well known in the art and includes but not limited to intravenous injection, intraperitoneal injection, intramuscular injection, intradermal administration or transdermal administration, etc. The term "animal" preferably refers to a mammal including rats, mice, cats, dogs, horses and sheep, etc. More preferably, this term refers to a human being.

EXAMPLES

The present invention will be described below in more detail with reference to the following examples. However, the scope of the invention is not limited by these examples.

Example 1

Preparation of "EGJV"

*Geum Japonicum thunb* was collected from Guizhou Province of China. The dried plant (1 kg) was powdered and percolated with methanol (8 L) at room temperature for 2-3 hours, repeated 5 times. The extract is then dried under reduced pressure to yield a residue about 50 grams. The dried powder (50 g) is suspended in 120 ml $H_2O$ and successively partitioned with hexane (5×250 ml), ethanol (5×250 ml) and n-Butanol (5×250 ml). The n-Butanol soluble fraction was filtered and evaporated under reduced pressure (50° C.) yielding a powdery residue. This powdery residue was applied on a column of Sephadex LH-20 equilibrated with 10% methanol and eluted with increasing concentration of methanol in water, 12 fractions were eluted containing mainly tannins such as gemins A, B, C, D, E and F, and triterpenes including 2-alpha,19-alpha-dihydroxy-3-oxo-12-ursen-28-oic acid, ursolic acid, epimolic acid, maslinic acid, euscaphic acid, tormentic acid, and 28-beta-D-glucoside of tormentic acid by NMR analysis. These 12 methanol-eluted fractions were combined and used as the EGJV evaluated in Examples 2 and 3.

During the course of screening for angiogenic and myogenic reagents from Chinese herbal medicine, the inventors of the present invention found that both the n-Butanol soluble fraction as well as the later methanol-eluted fractions show potent dual effects on stimulating early growth (less than 24 hours) of new vessels and muscle regeneration in severely damaged skeletal muscles. Otherwise indicated, the term "EGJV" used below refers to the methanol-eluted fractions.

Example 2

Evaluation of the Dual Effects of the Active Fraction on Rabbit Muscle Injury Model Here, the present inventors have tested the effect of the "EGJV". The experimental results surprisingly demonstrated that the EGJV has pronounced effects on the healing process of severely damaged skeletal muscle with the presence of regenerated muscle fibers in the damaged areas compared to fibrous scar tissue in the controls. The EGJV appears to have highly beneficial effects on stimulating both myogenesis and angiogenesis at early stage of the healing process of damaged muscle and on blocking fibrous scar formation both in skeletal muscle healing and skin wound healing.

The EGJV was used in severe muscle injury rabbit animal model (female, N=12, average body weight: 2.5 kg). The rabbits were subjected to strain-induced muscle injury created by a transection, with surgical scissors, on the tibialis anterior. Six rabbits were injected beneath the epidermis of tibialis anterior with 1 ml of the EGJV dissolved in 5% DMSO right after the strain-induced injuries. Six other rabbits were injected with an equal volume of 5% DMSO solution as control. The injection was only given once. Two rabbits from each group were sacrificed 2 days after the injury. The tibialis anterior was removed and processed for paraffin sectioning and HE (i.e. hemotoxylin and eosin) staining. Another two rabbits from each group were sacrificed one week after the injury and the remaining two rabbits from each group were sacrificed two weeks after the injury. All the sacrificed rabbits on different time points were processed following the same procedure.

As seen in FIG. 1E, after 1 day cut injury to the tibialis anterior with single injection of 5% DMSO, the field of the injury site was still fresh with almost no inflammatory cells infiltration and no newly formed vessels and regenerated myotubes were found. In contrast, the wound site was filled with a lot of inflammatory cells and some newly formed blood vessels with a few newly regenerated thin myotubes were found in the wound site in EGJV treated group on day 1 (FIG. 1B). Many newly formed blood vessels were observed in the wound site and some newly regenerated myotubes were also formed 2 days after the muscle injury (FIG. 1C). In contrast, the wound site was still fresh and there was almost no infiltration of inflammatory cells in DMSO control group (FIG. 1E). Neither newly formed blood vessels nor newly regenerated myotubes were observed (FIG. 1E) in this control group. Many newly regenerated and relatively matured myotubes (a bit smaller than normal myofibers with central nuclei) were observed in the gap of wound on day 18 in EGJV treated group (FIG. 1D). In contrast, the gap of wound in control was filled with fibrous tissue (FIG. 1F).

Example 3

Evaluation of the Dual Effects of the Active Fraction on Rat Muscle Injury Model The EGJV was further investigated in rat skeletal muscle injury model. The experimental results demonstrated that the EGJV could significantly stimulate revascularization (within 24 hours) and proliferation of satellite cells in the wound site of severely damaged muscles. Within two weeks of injury, the wound sites of EGJV treated animals were completely replaced by newly regenerated muscle fibers, in sharp comparison, fibrosis was the major feature in control animals.

The experimental rats (SD rat, female, N=40, average body weight: 150 g) were subjected to strain-induced muscle injury created by a transection, with surgical scissors, on the tibialis anterior. Twenty rats were injected beneath the epidermis of tibialis anterior with 0.1 ml of the EGJV dissolved in 5% DMSO right after the strain-induced injuries. Twenty other rats were injected with an equal volume of 5% DMSO solution as control. The injection was only given once. Four rats from each group were sacrificed 1, 2 and 3 days after the injury respectively. The tibialis anterior was removed and processed for paraffin sectioning and HE staining. Another four rats from each group were sacrificed 7 days after the injury and the remaining four rats from each group were sacrificed 14 days after the injury. All the sacrificed rats on different time points were processed following the same procedure.

The wound site in the tibialis anterior of control rats was filled with numerous inflammatory cells when examined 1 day after injury and more inflammatory cells were infiltrated on day 2 (FIG. 2a). Very few newly formed blood vessels were also observed. In contrast, numerous newly formed blood vessels on day 1 (FIG. 2b), and more blood vessels with newly regenerated long but thin myotubes (with nuclei present in the center of the myotubes) on day 2 (FIG. 2c) were evident at the wound site in EGJV-treated rats. Many more newly regenerated myotube clusters were observed replacing the damaged muscle fibres in the wound sites on day 3 in EGJV-treated group (FIG. 2d).

On day 7, the wound sites in the control animals were full of inflammatory cells and fibrous tissue replacement (FIG. 3a). In sharp contrast, a number of newly-developed, highly-aligned myotubes were observed in the wound site of EGJV treated animals (FIG. 3b-3c). Some proliferated satellite cells were also detected along the newly regenerated myotubes (FIG. 3d). No significant signs of fibrosis is observed either.

On day 14, the wound sites of control animals healed through fibrosis. The gaps of the muscle injuries were contracted as shown in FIG. 4a. However, in the EGJV treated rats, there were no signs of fibrosis and highly aligned newly regenerated muscle fibers bridged the wound site (FIG. 4b & 4c). The contour of the incision made in the muscle of experimental rats could still be recognized by the differentially stained muscle fibers between pre-existing muscle fibers and newly regenerated muscle fibers (FIG. 4b & 4c), probably due to the content difference of the proteins between the two different staged muscle fibers.

In summary, our experimental results showed that there was active neo-vascularization at the wound sites of skeletal muscle induced by a single local injection of EGJV and many new capillary sprouts filled with blood cells were formed around the injection sites within 24 hours after injury. In addition to many newly formed vessels, a number of scattered newly regenerated myotubes (long and thin) were also observed in the wound sites 2 days after the muscle damage. In contrast, many inflammatory cells were infiltrated in the control. On day 7, the newly regenerated muscle fibers became elongated and correctly orientated along the long axis of adjacent intact muscle fibers filling up the gap of the damaged muscles. While in the control, except for the infiltrated inflammatory cells, fibrous tissue formed in the wound site. On day 14, the wound of the damaged muscles was completely replaced by newly regenerated muscle in the EGJV-treated muscles, while in the control, the wound was healed with fibrosis and the wound gap was contracted.

Explanation of the Experimental Results

The experimental results indicate that the EGJV of the present invention interferes with the skeletal muscle healing process with its multiple effects on early angiogenesis (less than 24 hours), myogenesis and blocking fibrosis during the healing process of severely damaged muscle. The multiple effects of early angiogenesis, myogenesis and blocking fibrosis derived from the EGJV harmonize with each other, leading to complete healing of severely damaged skeletal muscles. The harmonization between early angiogenesis, myogenesis and inhibition of fibrosis constructs a more ideal surrounding environment for new muscle growth. Fibrous tissue can grow at a relatively ischemic condition. For instance, if the necessary nutrient elements are not supplied, good myogenesis will not be possible. If blood supply is insufficient, fibrous tissue can grow but normal tissue cells will not. Myogenesis can occur properly only in the condition of good blood supply and no fibrous tissue blockage. Our EGJV can stimulate the rapid growth of new vessels in 24 hours or less, therefore build up good condition for right cell to grow and proliferate. It has been demonstrated that the harmony of the enhanced early angiogenesis, myogenesis and blocking fibrosis has led complete healing of severely damaged muscles.

INDUSTRIAL APPLICABILITY OF THE INVENTION

The unique feature of the EGJV on rapid angiogenesis, myogenesis and blocking fibrosis makes it very useful for the treatment of skeletal muscle injury, soft tissue trauma, operation cut, burn, ulcers, bone fractures and bone defects. The EGJV can also be combined with other therapeutic drugs to form even better drugs, such as combining of the EGJV with oesteo-inductive proteins for the treatment of bone fractures and defects, especially at the location with less blood supply or most of the blood vessels being damaged. Therefore, EGJV has great potential to be developed into the first generation of therapeutic drugs for the treatment of skeletal muscle injuries, skin injuries, operation cut healing and bone fracture healing.

We claim:

1. A method for treating skeletal muscle injuries in an animal, comprising administering to the animal suffering from skeletal muscle injuries an effective amount of an organic extract from *Geum Japonicum thunb* var. comprising tannins wherein the tannins comprise gemins A, B, C, D, E and F and triterpenes comprising 2-hydroxyoleanolic acid, 2-hydroxylursolic acid, 2,19-dihydroxy-ursolic acid, 2-alpha,19-alpha-dihydroxy-3-oxo-12-ursen-28-oic acid, ursolic acid, epimolic acid, maslinic acid, euscaphic acid, tormentic acid, and 28-beta-D-glucoside of tormentic acid.

2. The method of claim 1, wherein the animal is a mammal.

3. The method of claim 2, wherein the mammal is a human.

* * * * *